(12) United States Patent
Petculescu

(10) Patent No.: US 10,416,120 B2
(45) Date of Patent: Sep. 17, 2019

(54) SYSTEM AND METHODS FOR DETERMINING SENSITIZATION OF ALLOY BY MEASURING AND CORRELATING ULTRASONIC PARAMETERS

(71) Applicant: University of Louisiana at Lafayette, Lafayette, LA (US)

(72) Inventor: Gabriela Petculescu, Lafayette, LA (US)

(73) Assignee: University of Louisiana at Lafayette, Lafayette, LA (US)

( * ) Notice: Subject to any disclaimer, the term of this patent is extended or adjusted under 35 U.S.C. 154(b) by 336 days.

(21) Appl. No.: 14/839,321

(22) Filed: Aug. 28, 2015

(65) Prior Publication Data

US 2016/0061781 A1    Mar. 3, 2016

Related U.S. Application Data

(60) Provisional application No. 62/043,611, filed on Aug. 29, 2014.

(51) Int. Cl.
*G01N 29/11* (2006.01)
*G01N 29/44* (2006.01)
(Continued)

(52) U.S. Cl.
CPC .......... *G01N 29/11* (2013.01); *G01N 29/043* (2013.01); *G01N 29/07* (2013.01); *G01N 29/12* (2013.01);
(Continued)

(58) Field of Classification Search
CPC ...... G01N 29/11; G01N 29/043; G01N 29/07; G01N 29/12; G01N 2291/0289;
(Continued)

(56) References Cited

U.S. PATENT DOCUMENTS

| 4,026,157 A | 5/1977 | Goebbels |
| 4,098,129 A | 7/1978 | Deblaere et al. |

(Continued)

FOREIGN PATENT DOCUMENTS

| WO | 2013009882 A2 | 1/2013 | |
| WO | WO 2013162521 A1 * | 10/2013 | ............. G01N 29/12 |

OTHER PUBLICATIONS

Labyed, Yassin, and Timothy A. Bigelow. "A Theoretical Comparison of Attenuation Measurement Techniques from Backscattered Ultrasound Echoes." The Journal of the Acoustical Society of America 129.4 (2011): 2316-2324.*

(Continued)

*Primary Examiner* — Natalie Huls
*Assistant Examiner* — Monica S Young
(74) *Attorney, Agent, or Firm* — Valauskas Corder LLC

(57) ABSTRACT

The present invention relates generally to a system and methods for testing sensitization of alloy nondestructively. More specifically, the present invention relates to a system and methods for determining the sensitization of an alloy by measuring ultrasonic parameters of the alloy using ultrasonic techniques, and correlating the measured ultrasonic parameters. In certain embodiments, the ultrasonic measuring techniques include pulse-echo and resonant ultrasound spectroscopy. Certain embodiments use ultrasonic measuring techniques to measure shear-wave velocity, compressional-wave velocity, and attenuation coefficient of compressional waves. One preferred embodiment correlates measured ultrasonic parameters including shear-wave velocity, compressional-wave velocity, and attenuation coefficient of compressional waves to determine the sensitization of alloy. Advantageously, certain embodiments of the invention make it easier to collect, store, and correlate measured ultrasonic parameters through use of a computer system.

17 Claims, 6 Drawing Sheets

(51) Int. Cl.
*G01N 29/04* (2006.01)
*G01N 29/07* (2006.01)
*G01N 29/12* (2006.01)
*G01N 29/46* (2006.01)

(52) U.S. Cl.
CPC .............. *G01N 29/44* (2013.01); *G01N 29/46* (2013.01); *G01N 2291/011* (2013.01); *G01N 2291/015* (2013.01); *G01N 2291/0234* (2013.01); *G01N 2291/0289* (2013.01)

(58) Field of Classification Search
CPC .. G01N 29/44; G01N 29/46; G01N 2291/011; G01N 2291/015; G01N 2291/0234
USPC .......................................................... 73/597
See application file for complete search history.

(56) References Cited

U.S. PATENT DOCUMENTS

| | | | |
|---|---|---|---|
| 4,100,808 A | 7/1978 | Evans et al. | |
| 4,165,649 A * | 8/1979 | Greer, Jr. | G01N 29/28 73/644 |
| 4,215,583 A | 8/1980 | Botsco et al. | |
| 4,539,848 A | 9/1985 | Takafuji et al. | |
| 4,893,510 A | 1/1990 | Ichikawa et al. | |
| 5,038,787 A | 8/1991 | Antich et al. | |
| 5,176,033 A * | 1/1993 | Jones | G01N 29/07 73/597 |
| 5,631,424 A * | 5/1997 | Nieters | G01N 29/0609 73/588 |
| 6,266,983 B1 | 7/2001 | Takada et al. | |
| 7,246,522 B1 * | 7/2007 | Diaz | G01N 29/07 73/52 |
| 2002/0035872 A1 * | 3/2002 | Lamouche | G01N 29/2418 73/643 |
| 2006/0201252 A1 * | 9/2006 | Georgeson | G01N 29/041 73/641 |
| 2007/0006651 A1 * | 1/2007 | Kruger | G01N 29/11 73/579 |
| 2009/0007678 A1 * | 1/2009 | Fukutomi | G01N 29/069 73/598 |
| 2014/0290808 A1 * | 10/2014 | Sharman | C21D 10/00 148/527 |
| 2015/0114121 A1 * | 4/2015 | Takahashi | G01N 29/045 73/579 |
| 2015/0300993 A1 * | 10/2015 | Prest | G01N 29/12 148/508 |
| 2017/0023532 A1 * | 1/2017 | Volker | G01N 29/024 |

OTHER PUBLICATIONS

Derivative and Instantaneous Velocity ("Derivative and Instantaneous Velocity", Notre Dame. www3.nd.edu/~apilking/Math10170/Information/Lectures/Lecture_3_ Derivatives_and_instantaneous_velocity%20copy.pdf Apr. 28, 2016.*
Bailey, Aaron J., Measuring Sensitization of AA 5083 Using Resistivity, Nonlinear Acoustics, and Attenuation, Apr. 1-10, 2011. LINK: http://vsgc.odu.edu/src/SRC2011/Undergrad%20Papers/Bailey,%20Aaron%20-%20%20Conference%20Paper.pdf.
Nanekar, PP et al., Advanced Ultrasonics for In-service Inspection of Nuclear Plants, LINK: http://www.igcar.ernet.in/events/inde2007/INDE%20presentations/P.P.Nanekar-Advanced%20Ultrasonic_Inspection%20Nuclear%20Plants.pdf.
Internet web site http://adsabs.harvard.edu—Technical paper on intergranular corrosion of aluminum alloys LINK: http://adsabs.harvard.edu/abs/2011PhDT . . . 216B.
Internet web site http://www.science.gov—A listing of government articles related to aluminum alloys LINK: http://www.science.gov/topicpages/a/aa5xxx+aluminum+alloys.html#.
Internet web site www.sciencedirect.com—Teaches testing of aluminum 5xxx alloys using UT inspection LINK: http://www.sciencedirect.com/science/article/pii/S0041624X10001952.

* cited by examiner

SYSTEM AND METHODS FOR DETERMINING SENSITIZATION OF ALLOY BY MEASURING AND CORRELATING ULTRASONIC PARAMETERS

CROSS REFERENCE TO RELATED PATENTS

This application claims the benefit of U.S. Provisional Patent Application No. 62/043,611 filed 29 Aug. 2014, which is incorporated by reference.

FIELD OF THE INVENTION

The present invention relates generally to a system and methods for testing sensitization of alloy. More specifically, the present invention relates to a system and methods for determining the sensitization of an alloy by measuring ultrasonic parameters of the alloy using ultrasonic techniques, and correlating the measured ultrasonic parameters. In certain embodiments, the ultrasonic measuring techniques include pulse-echo, resonant ultrasound spectroscopy, and piezoelectric acoustic transducer techniques. Certain embodiments use ultrasonic measuring techniques to measure shear-wave velocity, compressional-wave velocity, and attenuation coefficient of compressional waves. One preferred embodiment correlates measured ultrasonic parameters including shear-wave velocity, compressional-wave velocity, and attenuation coefficient of compressional waves to determine the sensitization of alloy. Advantageously, certain embodiments of the invention make it easier to collect, store, and correlate measured ultrasonic parameters through use of a computer system.

BACKGROUND OF THE INVENTION

An alloy is generally a mixture of metal elements, or a mixture of metal and other nonmetal elements. Examples of alloys include steel, solder, brass, etc. made by mixing two or more elements in a molten state to form a molten mixture. When the molten mixture cools, the alloy precipitates as solid crystallites. In polycrystalline form, the crystallites are small (microscopic) and do not form a perfect interface, rather a discontinuity forms between crystals. The transition between solid crystallites of the alloy is known as the grain boundary. Grain boundaries can exist throughout a formed alloy. After formation, certain alloys that are exposed to heat undergo what is termed "sensitization".

Exposure to environmental heat of metastable alloys causes specific atoms in that alloy to migrate to grain boundaries in the alloy to form a stable phase. The migration of atoms to grain boundaries eventually causes the grain boundaries to have different physical and chemical characteristics from the portion of the alloy not located at grain boundaries. Sensitization is the migration of a specific kind of atoms to grain boundaries in an alloy where a new phase (crystalline structure) is formed, different than what may have been intended for the homogeneous alloy. If the phase is corrosive, sensitization in an alloy causes it to become susceptible to intergranular corrosion.

Intergranular corrosion is a form of corrosion that affects the grain boundaries of an alloy. If a sufficient amount of intergranular corrosion occurs, then the alloy may undergo more detrimental forms of corrosion, for example, exfoliation corrosion and stress-corrosion cracking. Exfoliation corrosion is a form of corrosion that causes the complete separation of layers of the alloy. Stress-corrosion cracking is a form of corrosion that causes an incipient crack in the alloy to grow under mechanical stress. Exfoliation corrosion and stress-corrosion cracking are advanced forms of intergranular corrosion which may lead to the structural failure of the alloy. Structural failure resulting from intergranular corrosion may be avoided by early detection of sensitization.

Methods have been developed to measure sensitization for various alloys based on the change in chemical characteristics of the alloys. For example, sensitization of steel may be tested using an oxalic acid test, a ferric sulfate-sulfuric acid test, a nitric acid test, and copper-copper sulfate-50% sulfuric acid test. For aluminum alloys, sensitization may be tested by immersion tests in sodium chloride hydrogen peroxide solution, and by a nitric acid mass lost test. Generally, these tests may be difficult to use, are time consuming, they destroy the alloy tested, and require the use of dangerous chemicals.

Alternatively, ultrasonic testing can measure sensitization of an alloy nondestructively (not affecting the test piece) based on the change in physical characteristics of the alloy. Ultrasonic testing is generally nondestructive, and may be safer, easier to use, and quicker than tests based on the change in chemical characteristics. Determining sensitization using ultrasonic testing is done by transmitting ultrasonic waves through the alloy and measuring the velocity and attenuation of the received waves. The two types of waves measured are compressional-waves and shear-waves. A change to the physical characteristics of an alloy can cause ultrasonic waves to scatter and/or be absorbed differently, as well as travel with different velocities. As the atomic bonds change with the structure, the elastic moduli of the alloy change, and, with them, the sound velocities change. The combined effect of scattering and absorption is called attenuation. The velocity and attenuation of the propagating waves are dependent on the degree of physical change to the alloy and are consequently valuable ultrasonic parameters or determining sensitization.

Ultrasonic testing may be performed with the use of various devices including ultrasonic transducers. The configurations of these devices can vary, but generally fall into two basic categories called active transducers and passive transducers. An active transducer is a device that converts alternating electrical field into mechanical waves, and in reverse, converts mechanical waves into alternating electrical current. Passive transducers only convert incoming mechanical waves into alternating electrical current. Both active transducers and passive transducers can be made of piezoelectric crystals which generate voltage when they change shape by being stressed mechanically. Ultrasonic testing can be performed in various configurations with ultrasonic transducers in a variety of measuring methods. The combination between ultrasonic devices used and measuring methods is called an ultrasonic measuring technique.

One example of an ultrasonic measuring technique is a pulse-echo technique ("PE"). PE uses an active transducer that is coupled to the surface of the alloy tested, The transducer transmits pulses which pass through the alloy and are reflected by interfaces (such as solid-gas or solid-liquid). The returned ultrasonic pulses are converted into electrical signals by the same transducer working in reverse mode.

Another example of an ultrasonic measuring technique is a resonant ultrasound spectroscopy technique ("RUS"), that acts like a biopsy test. With the RUS, a small amount of alloy (e.g., 8 millimeters cube) is mechanically coupled between two piezoelectric transducers. The first transducer generates ultrasonic waves directed at the alloy. The second transducer is a passive transducer and detects the sample alloy's resonance.

In another ultrasonic measuring technique, an electromagnetic acoustic transducer technique ("EMAT") is used to test sensitization ultrasonically. EMAT uses a transmitted pulse and the receipt of a reflected pulse similar to PE. However, the active transducer used in EMAT is not mechanically coupled to the alloy.

Because the methods currently used to measure sensitization of alloys based on chemical reactions are difficult to use, time consuming, destroy the alloy tested, and require the use of dangerous chemicals, and because the methods may be unreliable and have errors associated with testing, there is a demand for a safer, easier-to-use, nondestructive, and accurate test for determining the sensitization of alloys.

The present invention satisfies the demand by providing a safer and easier-to-use test capable of accurately determining the sensitization of alloys without destroying the tested alloys.

SUMMARY OF THE INVENTION

The present invention is a system and methods for ultrasonically determining sensitization of alloys. Certain preferred embodiments of the present invention include a system which uses a PE ultrasonic technique to measure ultrasonic parameters of an alloy. The PE ultrasonic technique uses an active transducer that is mechanically coupled to the surface of the alloy. The transducer transmits pulses which pass through the alloy and are reflected by the opposite interface. The reflected pulses are detected, transformed into an electrical signal, and converted into ultrasonic parameters. The ultrasonic parameters are collected and stored on a computer system.

Alternative embodiments of the present invention include a system which uses a RUS ultrasonic technique to measure ultrasonic parameters. RUS ultrasonic technique uses two ultrasonic transducers. With the RUS ultrasonic technique, a small amount of the alloy is mechanically coupled between two transducers. The first transducer generates ultrasonic waves directed at the alloy. The second transducer is a passive transducer and detects the alloy's resonance. The resonance is transformed into an electrical signal, and converted to ultrasonic parameters. The ultrasonic parameters are collected and stored on a computer system.

Alternative embodiments of the present invention include a mobile system which uses PE and RUS ultrasonic techniques to measure ultrasonic parameters. RUS ultrasonic technique uses two ultrasonic transducers. With the RUS ultrasonic technique, a small amount of the alloy is mechanically coupled between two transducers. The first transducer generates ultrasonic waves directed at the alloy. The second transducer is a passive transducer and detects the alloy's resonance. The resonance is transformed into an electrical signal and converted to ultrasonic parameters. The ultrasonic parameters are collected and stored on a computer system. The PE ultrasonic technique uses an active transducer that is mechanically coupled to the surface of the alloy. The transducer transmits pulses which pass through the alloy and are reflected by interfaces. The reflected pulses are detected, transformed into an electrical signal, and converted into ultrasonic parameters. The ultrasonic parameters are collected and stored on a computer system.

Certain preferred embodiments of the present invention include a method comprising the steps of detecting an ultrasonic signal, transforming the ultrasonic signal into an electrical signal, converting the electrical signal into ultrasonic parameters, and correlating the ultrasonic parameters. The detecting step and the transforming step are performed by a transducer. The converting step and the correlating step are performed by a computer system storage and a computer system processor. In some embodiments the detecting step and the transforming step are performed by a transducer used in a PE ultrasonic technique. In other embodiments the detecting step and the transforming step are performed by two transducers used in a RUS ultrasonic technique. In one embodiment, the detecting step and transforming step are performed by three transducers used in a PE and a RUS technique.

Certain preferred embodiments of the present invention include a system which uses a computer system to correlate ultrasonic parameters. The computer system retrieves ultrasonic parameters stored in memory and uses a processor to correlate the difference between ultrasonic parameters. The ultrasonic parameters correlated are measured at the same time and measured for the same alloy. In additional embodiments, the ultrasonic parameters correlated are measured at different times and are measured for the same alloy. In some embodiments, the ultrasonic parameters correlated are measured at the same time and are measured for different alloys.

One object of the present invention is to provide a new test for ultrasonically and nondestructively determining sensitization of alloys.

A further object of this invention is to provide a system and methods for ultrasonically determining sensitization of alloys with improved accuracy and precision by correlating measured more than one ultrasonic parameter including compressional-wave velocity, shear-wave velocity, and the attenuation coefficient of compressional waves.

Another object of the present invention is to provide a system and methods for ultrasonically determining sensitization of alloys without destroying the tested alloys by using ultrasonic measurement techniques.

An additional object of this invention is to provide a safer and easier-to-use system and methods for ultrasonically determining sensitization of alloys by collecting, storing, and correlating ultrasonic parameters using a computer system.

The present invention, its attributes and advantages will be further understood with reference to the detailed description of presently contemplated embodiments, taken in conjunction with the accompanying drawings.

BRIEF DESCRIPTION OF THE DRAWINGS

The preferred embodiments of the invention will be described in conjunction with the appended drawings provided to illustrate and not to limit the invention, where like designations denote like elements, and in which.

DETAILED DESCRIPTION

Figure 1:
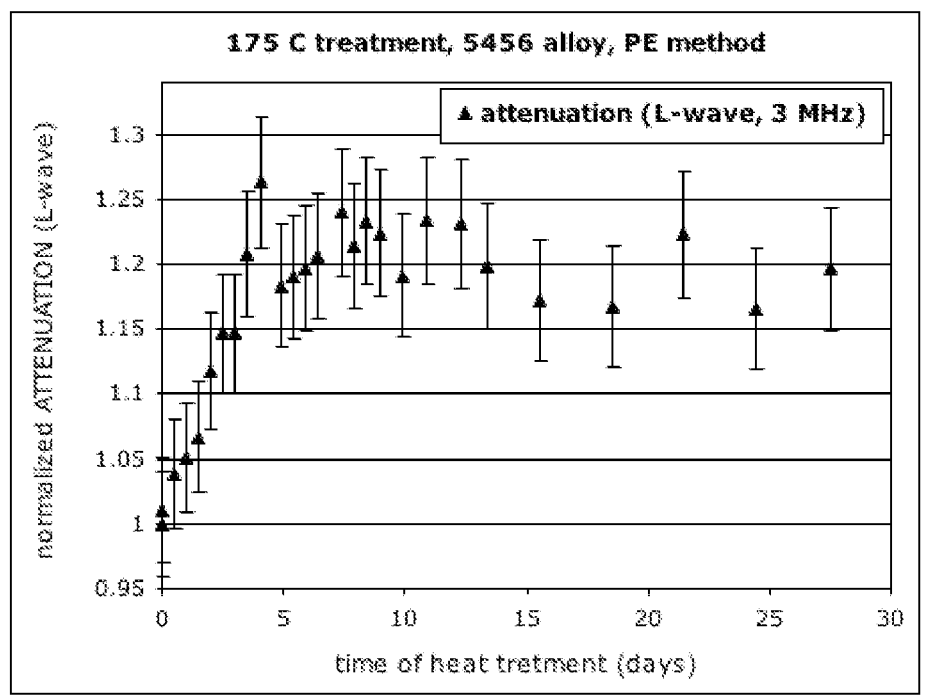
FIG. 1 illustrates a graph of ultrasonic parameters measured using a preferred embodiment of the present invention.

In the following description, for purposes of explanation, specific numbers, materials, and configurations are set forth in order to provide a thorough understanding of the invention. It will be apparent, however, to one having ordinary skill in the art that the invention may be practiced without these specific details. In some instances, well-known features may be omitted or simplified so as not to obscure the present invention. Furthermore, reference in the specification to "one embodiment" or "an embodiment" means that a particular feature, structure or characteristic described in connection with the embodiment is included in at least one embodiment of the invention. The appearances of the phrase "in one embodiment" in various places in the specification are not necessarily all referring to the same embodiment.

The present invention is a system and methods for ultrasonically determining sensitization of alloys. In one preferred embodiment, the invention is a system for determining the sensitization of an alloy, comprising: one or more ultrasonic measuring techniques for measuring the ultrasonic parameters of the alloy to obtain measured ultrasonic parameters of the alloy, and a computer system for collecting, storing, and correlating the measured ultrasonic parameters of the alloy. Some embodiments use one or more ultrasonic measuring techniques from the group of PE, RUS, and EMAT to measure ultrasonic parameters. The measured ultrasonic parameters include attenuation coefficient of compressional waves, shear-wave velocity, and compressional-wave velocity.

In another preferred embodiment, the invention is a method for determining the sensitization of an alloy, comprising the steps of: measuring ultrasonic parameters of the alloy with one or more ultrasonic measuring techniques to obtain measured ultrasonic parameters, and correlating the measured ultrasonic parameters of the alloy. In some embodiments, the measuring step includes one or more ultrasonic measuring techniques from the group of PE, RUS, and EMAT. The correlating step is performed on attenuation coefficient of compressional waves, shear-wave velocity, and compressional-wave velocity.

In some embodiments, the invention is a system including a PE ultrasonic measuring technique used to measure ultrasonic parameters of an alloy, and computer system storage for collection and storage of measured ultrasonic parameters of the alloy. The measured ultrasonic parameters are retrieved from the computer system storage and correlated by a computer system processor. The measured ultrasonic parameters are attenuation coefficient of compressional waves, shear-wave velocity, and compressional-wave velocity, and the computer processor correlates the difference between the values. Alternatively, the system includes a RUS ultrasonic measuring technique to measure ultrasonic parameters. The RUS ultrasonic technique is also used with the PE ultrasonic measuring technique to measure the ultrasonic parameters.

In some embodiments, the invention is a method comprising the steps of detecting an ultrasonic signal from an alloy using a transducer in a PE ultrasonic measuring technique, transforming the ultrasonic signal into an electrical signal using the transducer in the PE ultrasonic measuring technique, converting the electrical signal into measured ultrasonic parameters using a computer system processor, and correlating the measured ultrasonic parameters using the computer system processor.

In some embodiments the detecting step and the transforming step are performed by a transducer used in a PE ultrasonic technique. In other embodiments the detecting step and the transforming step are performed by two transducers used in a RUS ultrasonic technique. In one embodiment, the detecting step and transforming step are performed by three transducers used in a PE and a RUS technique.

Measured ultrasonic parameters illustrated in FIG. 1-7 were obtained for alloys which had sensitization accumulated over a period of time. PE is used to measure ultrasonic parameters of an alloy to obtain the measured ultrasonic parameters of the alloy. When PE is used to measure the ultrasonic parameters of the alloy, ultrasonic time trace of bottom-reflected pulses with a minimum of five pulses is used. Time-of-flight is the time of arrival of a given $n^{th}$ pulse. Distance traveled is given by $2(n-1)d$, where n represents the reflected pulse index (n=2 for the second pulse, n=3 for the third pulse, etc.), and d is the thickness of the sample. Velocity of the alloy measured is calculated as the slope of the linear fit of distance traveled vs. time-of-flight. Attenuation coefficient of the alloy is calculated as the slope of the linear fit of the natural log of the ratio of consecutive pulse amplitudes, $\ln(V_{n+1}/V_n)$, vs. distance traveled.

Alternatively, RUS is used with PE to measure the ultrasonic parameters of the alloy. In this instance, RUS is used on a biopsy-like sample (millimeter-size) to determine the velocity, which is to be used with time-of-flight data from PE to determine the thickness d, if not known. Once d is known, all subsequent measurements of velocity and attenuation are performed with PE as described above. If the thickness d is known, the additional determination of velocity with RUS is combined with that measured with PE for higher accuracy measurements. The measured ultrasonic parameters of the alloy are collected and stored by a computer system.

Figure 2:
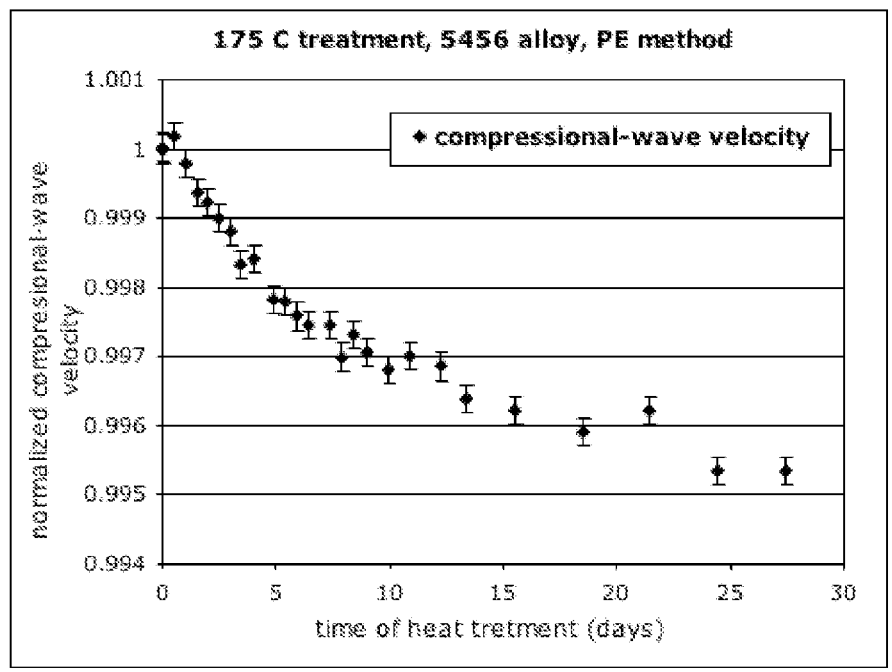
FIG. 2 illustrates a graph of different ultrasonic parameters measured using a preferred embodiment of the present invention.
Figure 3:
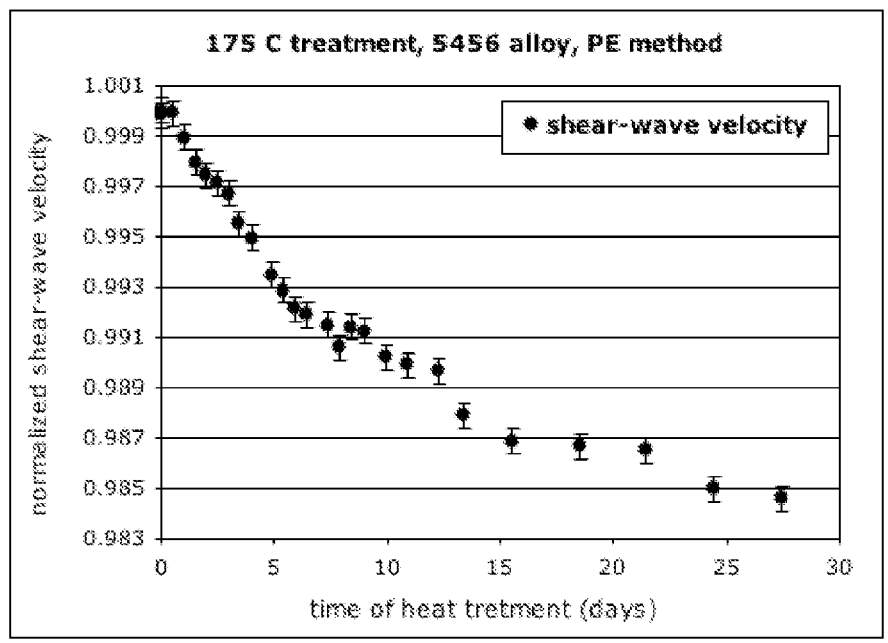
FIG. 3 illustrates a graph of different ultrasonic parameters measured using a preferred embodiment of the present invention.
Figure 4:
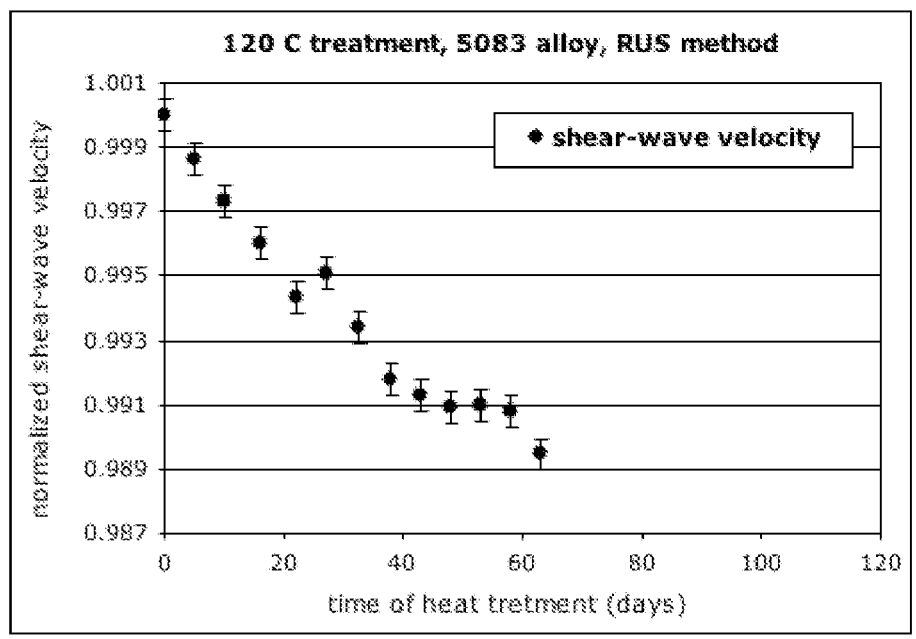
FIG. 4 illustrates a graph of ultrasonic parameters measured using an additional embodiment of the present invention.
Figure 5:
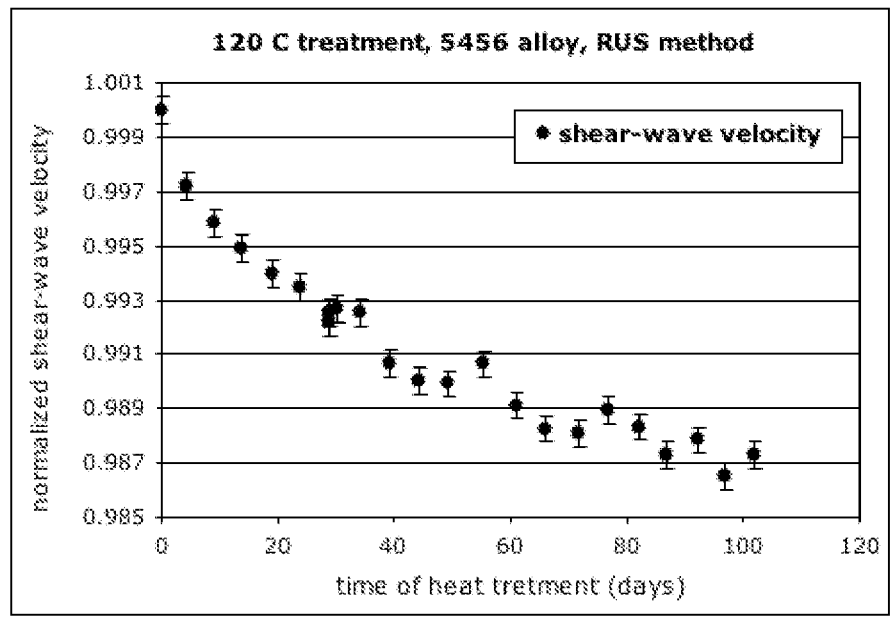
FIG. 5 illustrates a graph of ultrasonic parameters measured using an additional embodiment of the present invention.
Figure 6:
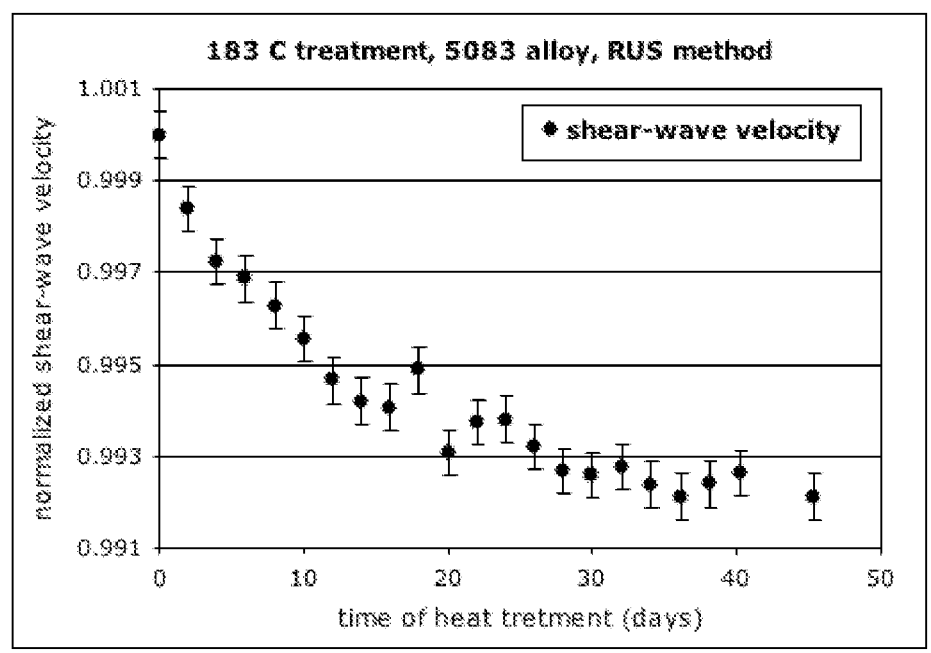
FIG. 6 illustrates a graph of ultrasonc parameters measured using an additional embodiment of the present invention.
Figure 7:
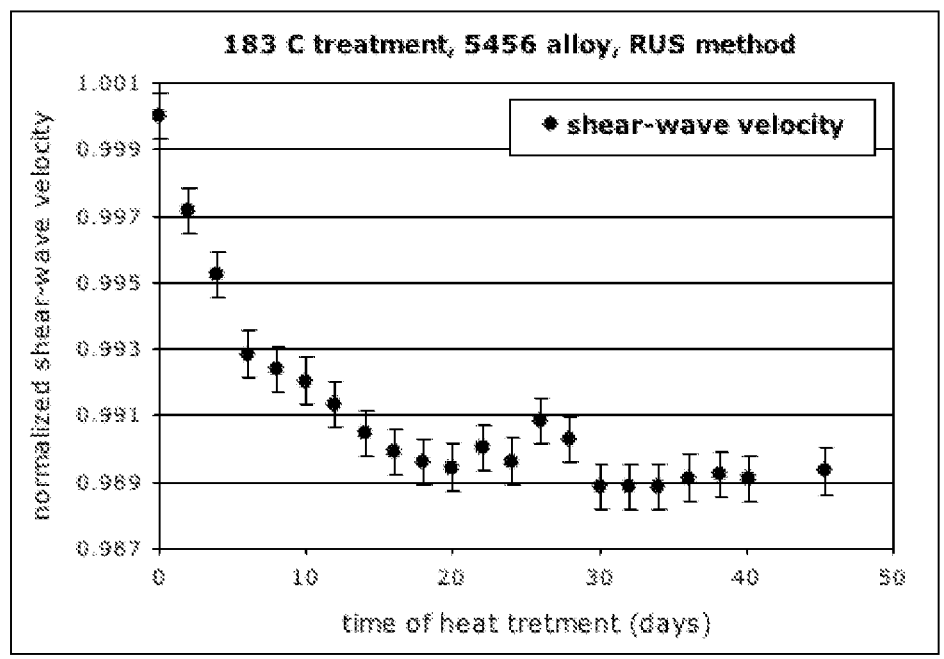
FIG. 7 illustrates a graph of ultrasonic parameters measured using an additional embodiment of the present invention.

In one embodiment, PE is used to measure the ultrasonic parameters of an alloy as the alloy undergoes sensitization over a period of time. The measured ultrasonic parameters are graphed as illustrated in FIG. 1-3. Each graph of measured ultrasonic parameters illustrated in FIG. 1-3 shows a different dependence on sensitization. The dependence on sensitization demonstrates that attenuation coefficient of compressional waves, shear-wave velocity, and compressional-wave velocity can be correlated to determine sensitization. Sensitization is determined by correlating the difference in measured ultrasonic parameters attenuation coefficient of compressional waves, shear-wave velocity, and compressional-wave velocity, which are measured at the same time for the alloy. In additional embodiments, measured ultrasonic parameters attenuation coefficient of compressional waves, shear-wave velocity, and compressional-wave velocity, which are measured at different times for an alloy are correlated to determine the change in sensitization for the same alloy.

Measured ultrasonic parameters of an alloy illustrated in FIG. 1-3 are correlated because compressional-wave velocity and shear-wave velocity decrease as sensitization increases, and a dependence on sensitization of measured ultrasonic parameters illustrated in FIG. 2 and FIG. 3 approaches zero as the alloy reaches full sensitization. The measured ultrasonic parameters illustrated in FIG. 2 and FIG. 3 show that compressional-wave velocity and shear-wave velocity reach full sensitization at approximately five days. Full sensitization shown by the measured ultrasonic parameters illustrated in FIG. 2 and FIG. 3 correlates with full sensitization shown by the measured ultrasonic parameters illustrated in FIG. 1, occurring at approximately five days. Correlating the measured ultrasonic parameters illustrated in FIG. 1-3 at approximately five days quantitatively determines sensitization because the measured ultrasonic parameters are equivalent to sensitization found using the published NAMLT standard of approximately 53 mg/cm$^2$.

Figure 8:
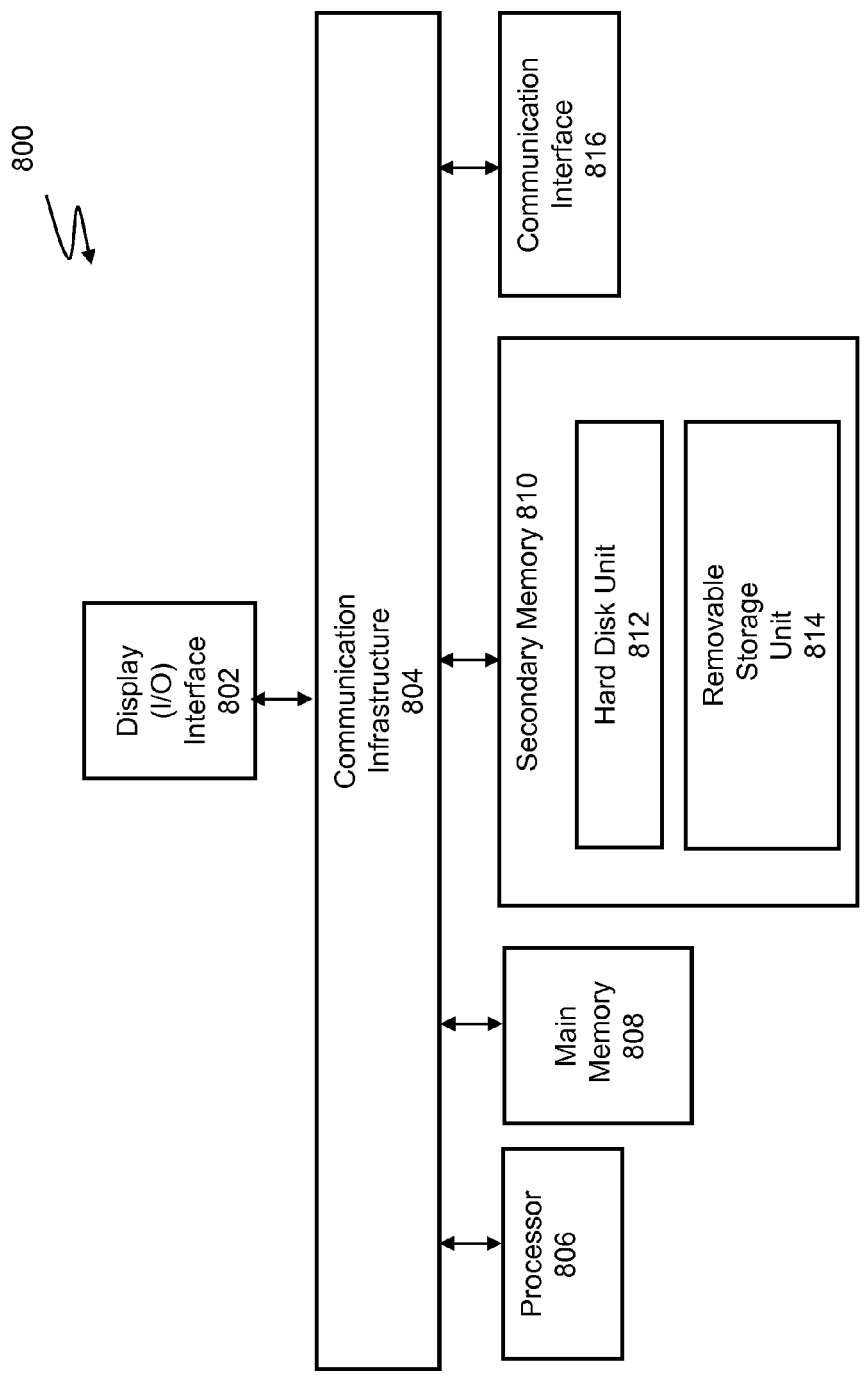
FIG. 8 illustrates an exemplary computer system used with an embodiment of the present invention.

FIG. 8 illustrates an exemplary computer system 800 that may be used to implement the methods according to the invention.

Computer system 800 includes an input/output interface 802 connected to communication infrastructure 804—such as a bus—, which forwards data such as graphics, text, and information, from the communication infrastructure 804 or from a frame buffer (not shown) to other components of the computer system 800. The input/output interface 802 may be, for example, a display device, a keyboard, touch screen, joystick, trackball, mouse, monitor, speaker, printer, Google Glass® unit, web camera, any other computer peripheral device, or any combination thereof, capable of entering and/or viewing data.

Computer system 800 includes one or more processors 806, which may be a special purpose or a general-purpose digital signal processor configured to process certain information. Computer system 800 also includes a main memory 808, for example random access memory (RAM), read-only memory (ROM), mass storage device, or any combination thereof. Computer system 800 may also include a secondary memory 810 such as a hard disk unit 812, a removable storage unit 814, or any combination thereof. Computer system 800 may also include a communication interface 816, for example, a modem, a network interface (such as an Ethernet card or Ethernet cable), a communication port, a PCMCIA slot and card, wired or wireless systems (such as Wi-Fi, Bluetooth, Infrared), local area networks, wide area networks, intranets, etc.

It is contemplated that the main memory 808, secondary memory 810, communication interface 816, or a combination thereof, function as a computer usable storage medium, otherwise referred to as a computer readable storage medium, to store and/or access computer software including computer instructions. For example, computer programs or other instructions may be loaded into the computer system 800 such as through a removable storage device, for example, a floppy disk, ZIP disks, magnetic tape, portable flash drive, optical disk such as a CD or DVD or Blu-ray, Micro-Electro-Mechanical Systems (MEMS), nanotechnological apparatus. Specifically, computer software including computer instructions may be transferred from the removable storage unit 814 or hard disc unit 812 to the secondary memory 810 or through the communication infrastructure 804 to the main memory 808 of the computer system 800.

Communication interface 816 allows software, instructions and data to be transferred between the computer system 800 and external devices or external networks. Software, instructions, and/or data transferred by the communication interface 816 are typically in the form of signals that may be electronic, electromagnetic, optical or other signals capable of being sent and received by the communication interface 816. Signals may be sent and received using wire or cable, fiber optics, a phone line, a cellular phone link, a Radio Frequency (RF) link, wireless link, or other communication channels.

Computer programs, when executed, enable the computer system 800, particularly the processor 806, to implement the methods of the invention according to computer software including instructions.

The computer system 800 described may perform any one of, or any combination of, the steps of any of the methods according to the invention. It is also contemplated that the methods according to the invention may be performed automatically.

The computer system 800 of FIG. 8 is provided only for purposes of illustration, such that the invention is not limited to this specific embodiment. It is appreciated that a person skilled in the relevant art knows how to program and implement the invention using any computer system.

The computer system 800 may be a handheld device and include any small sized computer device including, for example, a personal digital assistant (PDA), smart hand-held computing device, cellular telephone, or a laptop or netbook computer, hand held console or MP3 player, tablet, or similar hand held computer device, such as an iPad®, iPad Touch® or iPhone®.

Figure 9:
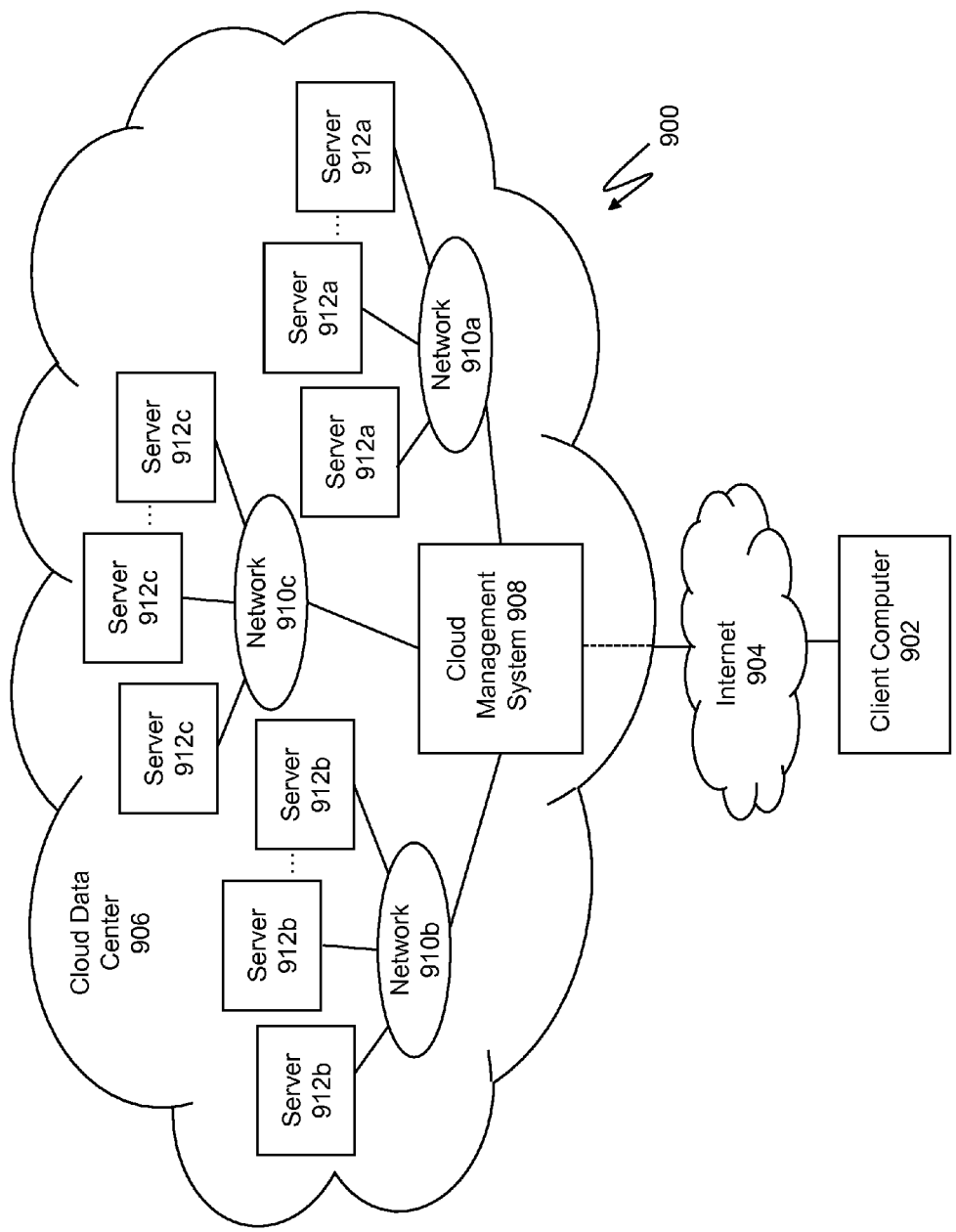
FIG. 9 illustrates an exemplary cloud computing system used with an embodiment of the present invention.

FIG. 9 illustrates an exemplary cloud computing system 900 that may be used to implement the methods according to the present invention. The cloud computing system 900 includes a plurality of interconnected computing environments. The cloud computing system 900 utilizes the resources from various networks as a collective virtual computer, where the services and applications can run independently from a particular computer or server configuration making hardware less important.

Specifically, the cloud computing system 900 includes at least one client computer 902. The client computer 902 may be any device through the use of which a distributed computing environment may be accessed to perform the methods disclosed herein, for example, a traditional computer, portable computer, mobile phone, personal digital assistant, tablet to name a few. The client computer 902 includes memory such as random access memory (RAM), read-only memory (ROM), mass storage device, or any combination thereof. The memory functions as a computer usable storage medium, otherwise referred to as a computer readable storage medium, to store and/or access computer software and/or instructions.

The client computer 902 also includes a communications interface, for example, a modem, a network interface (such as an Ethernet card), a communications port, a PCMCIA slot and card, wired or wireless systems, etc. The communications interface allows communication through transferred signals between the client computer 902 and external devices including networks such as the Internet 904 and cloud data center 906. Communication may be implemented using wireless or wired capability such as cable, fiber optics, a phone line, a cellular phone link, radio waves or other communication channels.

The client computer 902 establishes communication with the Internet 904—specifically to one or more servers—to, in turn, establish communication with one or more cloud data centers 906. A cloud data center 906 includes one or more networks 910a, 910b, 910c managed through a cloud management system 908. Each network 910a, 910b, 910c includes resource servers 912a, 912b, 912c, respectively. Servers 912a, 912b, 912c permit access to a collection of computing resources and components that can be invoked to instantiate a virtual machine, process, or other resource for a limited or defined duration. For example, one group of resource servers can host and serve an operating system or components thereof to deliver and instantiate a virtual machine. Another group of resource servers can accept requests to host computing cycles or processor time, to supply a defined level of processing power for a virtual machine. A further group of resource servers can host and serve applications to load on an instantiation of a virtual machine, such as an email client, a browser application, a messaging application, or other applications or software.

The cloud management system 908 can comprise a dedicated or centralized server and/or other software, hardware, and network tools to communicate with one or more networks 910a, 910b, 910c, such as the Internet or other public or private network, with all sets of resource servers 912a, 912b, 912c. The cloud management system 908 may be configured to query and identify the computing resources and components managed by the set of resource servers 912a, 912b, 912c needed and available for use in the cloud data center 906. Specifically, the cloud management system 908 may be configured to identify the hardware resources and components such as type and amount of processing power, type and amount of memory, type and amount of storage, type and amount of network bandwidth and the like, of the set of resource servers 912a, 912b, 912c needed and available for use in the cloud data center 906. Likewise, the cloud management system 908 can be configured to identify the software resources and components, such as type of Operating System (OS), application programs, and the like, of the set of resource servers 912a, 912b, 912c needed and available for use in the cloud data center 906.

The present invention is also directed to computer products, otherwise referred to as computer program products, to provide software to the cloud computing system 900. Computer products store software on any computer useable medium, known now or in the future. Such software, when executed, may implement the methods according to certain embodiments of the invention. Examples of computer useable mediums include, but are not limited to, primary storage devices (e.g., any type of random access memory), secondary storage devices (e.g., hard drives, floppy disks, CD ROMS, ZIP disks, tapes, magnetic storage devices, optical storage devices, Micro-Electro-Mechanical Systems (MEMS), nanotechnological storage device, etc.), and communication mediums (e.g., wired and wireless communications networks, local area networks, wide area networks, intranets, etc.). It is to be appreciated that the embodiments described herein may be implemented using software, hardware, firmware, or combinations thereof.

The cloud computing system 900 of FIG. 9 is provided only for purposes of illustration and does not limit the invention to this specific embodiment. It is appreciated that a person skilled in the relevant art knows how to program and implement the invention using any computer system or network architecture.

While the disclosure is susceptible to various modifications and alternative forms, specific exemplary embodiments of the invention have been shown by way of example in the drawings and have been described in detail. It should be understood, however, that there is no intent to limit the disclosure to the particular embodiments disclosed, but on the contrary, the intention is to cover all modifications, equivalents, and alternatives falling within the scope of the disclosure as defined by the appended claims.

The invention claimed is:

1. A method for determining sensitization of an alloy, wherein sensitization is a new phase at grain boundaries in the alloy, the method comprising the steps of:
   positioning one or more transducer on an alloy sample;
   transmitting by the one or more transducer an ultrasonic signal;
   detecting by the one or more transducer a reflected ultrasonic signal of the ultrasonic signal;
   transforming by the one or more transducer the reflected ultrasonic signal into an electrical signal;
   converting by a processor the electrical signal into measured ultrasonic parameters, wherein measured ultrasonic parameters include a shear-wave velocity, a compressional-wave velocity, and an attenuation coefficient of compressional waves, wherein said converting step further comprises the steps of: computing a distance traveled 2(n−1)d, wherein n represents a reflected pulse index and d is a thickness of the alloy sample, determining a velocity as a first slope of a first linear fit of the distance traveled versus a time of flight, wherein the time of flight is a time of arrival of the reflected ultrasonic signal, and calculating the attenuation coefficient as a second slope of a second linear fit of a natural log of a ratio of consecutive ultrasonic signal amplitudes $\ln(V_{n+1}/V_n)$ versus the distance traveled; and
   correlating by the processor the measured ultrasonic parameters to determine sensitization of the alloy sample, wherein both the compressional-wave velocity and the shear-wave velocity decrease and the attenuation coefficient increases as sensitization increases.

2. The method as disclosed in claim 1, wherein said detecting step is performed by a transducer in a PE ultrasonic measuring technique.

3. The method as disclosed in claim 1, wherein said detecting step is performed by two transducers in a RUS ultrasonic measuring technique.

4. The method as disclosed in claim 1, wherein said detecting step is performed by three transducers in PE and RUS ultrasonic measuring techniques.

5. The method as disclosed in claim 1, wherein said correlating step is performed on the alloy sample at different times.

6. The method as disclosed in claim 1, wherein the alloy sample is an aluminum alloy.

7. The method as disclosed in claim 1, wherein the alloy sample is a 5456 aluminum alloy.

8. The method as disclosed in claim 1, wherein the alloy sample is a 5083 aluminum alloy.

9. The method as disclosed in claim 1, wherein shear-wave velocity, compressional-wave velocity, and attenuation coefficient of compressional waves are measured at the same time.

10. The method as disclosed in claim 1, wherein the new phase is a crystalline material.

11. A system for determining sensitization of an alloy, wherein sensitization is a new phase at grain boundaries in the alloy, the system comprising:
    an alloy sample;
    one or more transducers positioned on the alloy sample, each transducer configured to transmit an ultrasonic signal and detect a reflected ultrasonic signal;
    a processor configured to use the reflected ultrasonic signal to measure ultrasonic parameters of the alloy sample, the measured ultrasonic parameters consisting of a shear-wave velocity, a compressional-wave velocity, and an attenuation coefficient of compressional waves, wherein the processor is further configured to measure ultrasonic parameters by computing a distance traveled 2(n−1)d, wherein n represents a reflected pulse index and d is a thickness of the alloy sample, determining a velocity as a first slope of a first linear fit of the distance traveled versus a time of flight, wherein the time of flight is a time of arrival of the reflected ultrasonic signal, and calculating the attenuation coefficient as a second slope of a second linear fit of a natural log of a ration of consecutive ultrasonic signal amplitudes $\ln(V_{n+1}/V_n)$ versus the distance traveled;

the processor further configured to correlate the measured ultrasonic parameters to determine sensitization of the alloy sample, wherein both the compressional-wave velocity and the shear-wave velocity decrease and the attenuation coefficient increases as sensitization increases; and a database configured to store the measured ultrasonic parameters of the alloy sample.

12. The system as disclosed in claim 11, wherein said one or more transducers is used in a PE ultrasonic measuring technique.

13. The system as disclosed in claim 11, wherein said one or more transducers is used in PE and RUS ultrasonic measuring techniques.

14. The system as disclosed in claim 11, wherein the alloy sample is an aluminum alloy.

15. The system as disclosed in claim 11, wherein the alloy sample is a 5456 aluminum alloy.

16. The system as disclosed in claim 11, wherein the alloy sample is a 5083 aluminum alloy.

17. The system as disclosed in claim 11, wherein the new phase is a crystalline material.

* * * * *